(12) United States Patent
Yacoub et al.

(10) Patent No.: US 10,034,837 B2
(45) Date of Patent: Jul. 31, 2018

(54) NANOPARTICLE DRUG DELIVERY

(71) Applicant: HEART BIOTECH PHARMA LIMITED, London (GB)

(72) Inventors: Magdi Habib Yacoub, London (GB); Ibrahim M. El-Sherbiny, 6th of October (EG)

(73) Assignee: HEART BIOTECH PHARMA LIMITED, London (GB)

( * ) Notice: Subject to any disclaimer, the term of this patent is extended or adjusted under 35 U.S.C. 154(b) by 0 days.

(21) Appl. No.: 15/191,570

(22) Filed: Jun. 24, 2016

(65) Prior Publication Data

US 2016/0374950 A1    Dec. 29, 2016

(30) Foreign Application Priority Data

Jun. 25, 2015  (GB) .................................. 1511210.5

(51) Int. Cl.
*A61K 31/192*  (2006.01)
*A61K 9/50*  (2006.01)
(Continued)

(52) U.S. Cl.
CPC .......... *A61K 9/5073* (2013.01); *A61K 9/0019* (2013.01); *A61K 9/0053* (2013.01);
(Continued)

(58) Field of Classification Search
CPC .......... A61K 9/51; A61K 9/50; A61K 31/192; A61K 31/4965; A61K 47/36
See application file for complete search history.

(56) References Cited

U.S. PATENT DOCUMENTS

| 2008/0286372 | A1 | 11/2008 | Pacetti et al. |
| 2011/0250134 | A1 | 10/2011 | Cabrales et al. |
| 2013/0084336 | A1 | 4/2013 | Friedman et al. |

FOREIGN PATENT DOCUMENTS

| GB | 2526897 A | 12/2015 |
| WO | 2006/084914 | 8/2006 |

(Continued)

OTHER PUBLICATIONS

Ei-Sherbiny et al , "COntrolled PUlmonary Asdministration of Curcumin USing Swellable Biocompatible Microparticle", Molecular Pharmacueitcs, vol. 9, No. 2, 2012, pp. 269-280.*

(Continued)

*Primary Examiner* — Carlos A Azpuru
(74) *Attorney, Agent, or Firm* — Saul Ewing Arnstein & Lehr LLP

(57) ABSTRACT

Therapeutic formulations are described for use in the treatment of chronic obstructive pulmonary disease, bronchial asthma, cystic fibrosis, chlorine inhalation, influenza and acute myocardial infarction. The formulations comprise polymeric nanoparticles or polymeric nanoparticles encapsulated within cross-linked polymeric hydrogel microparticles, wherein the polymeric nanoparticles carry a therapeutic agent suitable for treatment of chronic obstructive pulmonary disease, bronchial asthma, cystic fibrosis, chlorine inhalation, influenza, acute myocardial infarction and heart failure. Preferred formulations are inhalable, dry powder therapeutic formulations, which are able to swell on administration to the lungs of a patient.

19 Claims, 5 Drawing Sheets

(51) Int. Cl.
| | |
|---|---|
| A61K 31/4965 | (2006.01) |
| A61K 47/36 | (2006.01) |
| A61K 9/00 | (2006.01) |
| A61K 9/51 | (2006.01) |
| A61K 31/00 | (2006.01) |
| A61K 9/06 | (2006.01) |
| A61K 33/00 | (2006.01) |
| A61K 9/16 | (2006.01) |

(52) U.S. Cl.
CPC .............. *A61K 9/0075* (2013.01); *A61K 9/06* (2013.01); *A61K 9/5036* (2013.01); *A61K 9/5153* (2013.01); *A61K 9/5161* (2013.01); *A61K 31/00* (2013.01); *A61K 31/192* (2013.01); *A61K 31/4965* (2013.01); *A61K 33/00* (2013.01); *A61K 47/36* (2013.01); *A61K 9/0073* (2013.01); *A61K 9/1652* (2013.01)

(56) References Cited

FOREIGN PATENT DOCUMENTS

| | | |
|---|---|---|
| WO | 2011/092690 A1 | 8/2011 |
| WO | 2012148953 A1 | 11/2012 |
| WO | 2013/169538 A1 | 11/2013 |
| WO | 2013/190497 A2 | 12/2013 |

OTHER PUBLICATIONS

Extended European Search Report, dated Jan. 31, 2017, issued in corresponding European Application No. 16176026.9.
Search Report, dated Mar. 4, 2016 issued in priority GB Application No. GB1511210.5.
Cystic Fibrosis Trust (UK), UK Cystic Fibrosis Registry, Annual Data Report 2012., 2012.
Beckman, et al., "Nitric oxide, superoxide and peroxynitrite: the good, the bad and the ugly", American Journal of Physiology—Cell Physiology; 271(5):1424-1437, 1996.
Bolli, et al., "Cardioprotective function of inducible nitric oxide synthase and role of nitric oxide in myocardial ischemia and preconditioning: an overview of a decade of research", J Mol Cell Cardiol; 33:1897-918, 2001.
Cheow, et al., "Enhancing encapsulation efficiency of highly water-soluble antibiotic in poly(lactic-co-glycolic acid) nanoparticles: Modifications of standard nanoparticle preparation methods", Colloids and Surfaces a: Physiochemical ad Engineering Aspects, Elsevier, Amsterdam, NL, vol. 370, No. 1-3, pp. 79-86 XP027404123, Nov. 5, 2010.
Du, et al., "Swellable ciprofloxacin-loaded nano-in-micro hydrogel particles for local drug delivery.", AAPS PharmSciTech, 15(6):1535-44, 2014.
Dupuy, et al., "Bronchiodilator action of inhaled Nitric Oxide in Guinea Pigs", J Clin Inv; vol. 90, Aug. 1992:421-428, 1992.
El-Sherbiny, et al., "Biodegradable nano-micro carrier systems for sustained pulmonary drug delivery: (I) self-assembled nanoparticles encapsulated in respirable/swellable semi-IPN microspheres", Int J. Pharm 395: 132-141, 2010.
El-Sherbiny, et al., "Biodegradable pH-responsive alginate-poly (lactic-co-glycolic acid) nano/micro hydrogel matrices for oral delivery of silymarin", CarbohydrPolym, 83, 1345-1354, 2010.
El-Sherbiny, et al., "Controlled release pulmonary administration of curcumin using swellable biocompatible nano-microparticles systems", Molecular Pharmaceutics, 9(2), 269-280., 2012.
El-Sherbiny, et al., "Cryomilled physically cross-linked biodegradable hydrogel microparticles as novel potential carriers for inhalation therapy", Annual Meeting of American Association of Pharmaceutical Scientists, Los Angles, CA, AM-09-01692, 2009.

El-Sherbiny, et al., "Nano-micro carrier systems for sustained pulmonary drug delivery", Biomedical Engineering Society Annual Meeting (BMES), Austin, TX, 2010.
El-Sherbiny, et al., "Novel cryomilled physically cross-linked biodegradable hydrogel microparticles as carriers for inhalation therapy", J. Microencapsulation, 27(7): 561-572, 2010.
El-Sherbiny, et al., "Novel non-covalently cross-linked hydrogel nano-microparticles for inhalation therapy", Annual Meeting of American Association of Pharmaceutical Scientists, New Orleans, LA, 2010.
El-Sherbiny, et al., "Novel spray dried biodegradable semi-IPN hydrogel microspheres for pulmonary drug delivery", Annual Meeting of American Association of Pharmaceutical Scientists, Los Angles, CA, (AM-09-01708), 2009.
El-Sherbiny, et al., "PLGA nanoparticles encapsulated in respirable/swellable hydrogel microspheres as potential carriers for sustained drug delivery to the lung", Annual Meeting of American Association of Pharmaceutical Scientists, New Orleans, LA., 2010.
El-Sherbiny, et al., "Swellable microparticles as carriers for sustained pulmonary drug delivery", J. Pharm Sci, 99 (5): 2343-2356., 2010.
Fang, "Mechanisms of Nitric Oxide related antimicrobial activity", J Clin Inv, June; vol. 99(12):2818-2825, 1997.
Gaston, et al., "Endogenous nitrogen oxides and bronchiodilator S-nitrosothiols in human airways", PNAS, Dec. 1, 1993;vol. 90 (No. 23): 10957-10961, 1993.
Gunnarsson, et al., "The effects of inhalation of corticosteroids immediately after experimental chlorine gas lung injury", J Trauma; 48:101-7, 2000.
Heindenreich, et al., "Forecasting the impact of heart failure in the United States: a policy statement from the American Heart Association", Circ Heart Fail May 2013; 6(3):606-19, 2013.
Hezhong Chen, et al., "Paclitaxel-loaded poly(glycolide-co-[epsilon]-caprolactone)-b-D-[alpha]-tocopheryl polyethylene glycol 200 succinate nanoparticles for lung cancer therapy", International J. of Nanomedicine, pp. 1947 XP055315442, May 1, 2013.
Honavar, et al., "Nitrite Therapy improves survival postexposure to chlorine gas", Am J Phisiol, Dec. 2014; vol. 307: No. 11, L888-L894, 2014.
Kelley, "Inducible nitric oxide synthase expression is reduced in cystic fibrosis murine and human airway epithelial cells", J Clin Invest Sep. 15; 102(6): 1200-1207, 1998.
Meurs, et al., "Arginase and asthma: novel insights into nitric oxide homeostasis and airway hyperresponsiveness", Trends in Pharmacological Sciences. Sep. 2003; vol. 24(9): 450-455, 2003.
Regev-Shoshani, et al., "Gaseous nitric oxide reduces influenza infectivity in vitro", Nitric Oxide, May 2013; vol. 31: 48-53, 2013.
Rimelzwaan, et al., "Inhibition of Influenza Virus Replication by Nitric Oxide", J Virol Oct; 73(10):8880-8883, 1999.
Rubinstein, et al., "Modulation of airway epithelial cell ciliary beat frequency by Nitric Oxide", Biochemical & Biophysical Research Communications, Feb. 26, 1993; vol. 191(1): 83-88, 1993.
Schulz, et al., "Nitric Oxide in myocardial ischemia/reperfusion injury", Cardiovascular Research 61 (2004): 402-413, 2004.
Selvam, et al., "Swellable microparticles for sustained release drug delivery to the lung using propellant driven metered dose inhalers", Biomedical Engineering Society Annual Meeting (BMES), Austin, TX, 2010.
Stewart, et al., "Heart Failure and the ageing population: an increasing burden in the 21st century?", Heart Jan: 89 (1): 49-53, 2003.
Van Sickle, et al., "Acute health effects after exposure to chlorine gas released after a train derailment", Am J Emerg Med; 27:1-7, 2009.
World Health Organization, "(who.int). Monogenic diseases—cystic fibrosis".
Partial European Search Report, dated Nov. 3, 2016, issued in corresponding EP Application No. EP 16 17 6026.

\* cited by examiner

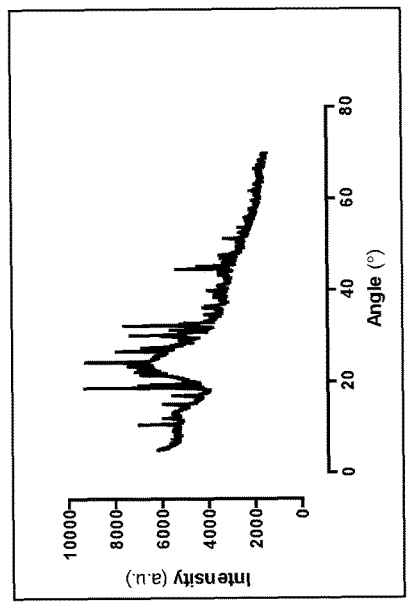
Figure 3(a)
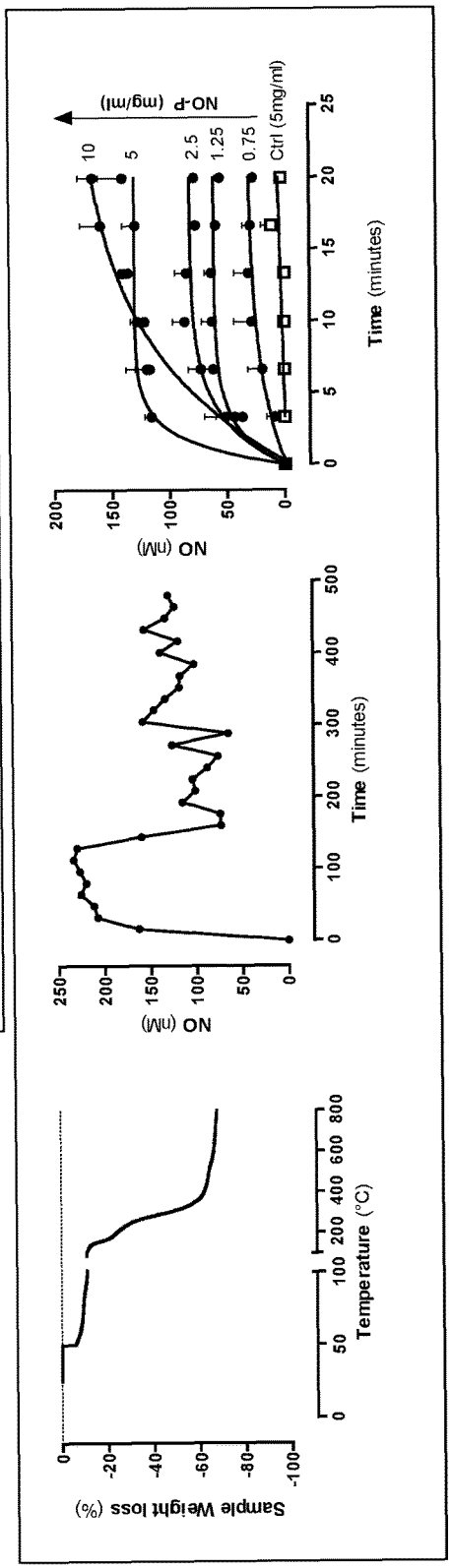
Figure 3(b)
Figure 3(c)
Figure 3(d)

NANOPARTICLE DRUG DELIVERY

CROSS-REFERENCE TO RELATED APPLICATIONS

This application is based on, and claims priority to United Kingdom Application No. GB1511210.5, filed Jun. 25, 2015, the entire contents of which is fully incorporated herein by reference.

FIELD OF THE INVENTION

The present invention relates to pharmaceutical formulations for the treatment of chronic obstructive pulmonary disease, bronchial asthma, cystic fibrosis, chlorine inhalation, influenza and myocardial infarction. Aspects of the invention relate to inhalable, dry powder formulations for pulmonary administration. Further aspects of the invention relate to formulations suitable for injectable or oral administration.

BACKGROUND TO THE INVENTION a. Chronic Obstructive Pulmonary Disease (COPD)

COPD is a collective name for a collection of lung diseases, which include chronic bronchitis, emphysema and chronic obstructive airways disease. People with COPD have difficulty breathing, primarily due to the narrowing of their airways. Symptoms are then often further compounded by bacterial infections and exaggerated inflammatory responses. More prevalent in men than in women, COPD is one of the most common respiratory diseases, affecting around 5% of the world population, and by some estimates is related to around 3% of global disability (WHO, Burden of COPD). COPD usually worsens gradually over time, and can ultimately result in death. Around 3 million people per annum die from COPD. There are no known cures, but symptoms are treatable, and progression can be delayed. Current therapies include bronchiodilators (β2 agonists and anticholinergics), corticosteroids, antibiotics, supplemental oxygen and in the most severe cases surgery, including lung transplantation.

In the form of Nitrosothiols (RS-NO), Nitric Oxide (NO) is known to possess a powerful bronchodilator effect in both humans and animals (Gaston et al., 1998; Dupuy et al., 1992). NO is also known to be beneficial in countering airway hyper-responsiveness (Meurs et al., 2003) and to possess powerful antimicrobial properties. The main challenge with NO therapy is in sustaining benefit over a prolonged period. There therefore exists a need to be able to provide a controlled, sustained release of NO.

b. Bronchial Asthma

Asthma is a common chronic inflammatory disease of the airways, affecting the bronchi. Caused by a combination of genetic and environmental factors (e.g. allergens), it affects around 300 million people worldwide, ranging from 1% to 18% of the population in different countries. While the prognosis for asthma is generally good, it causes moderate to severe disability in around 20 million people and kills around 300,000 per annum. 80% of these deaths occur in developing countries.

Airway hyper-responsiveness (AHR) is the main feature of Asthma, and is defined as an increase in the ease and degree of airway narrowing in response to broncho-constrictor stimuli. Several studies have demonstrated a positive effect of NO in influencing and reducing AHR induced by different mediators (Meurs et al., 2003). It is thought the NO counteracts smooth muscle contraction in the bronchia in response to spasmogens. Again there exists a need in the treatment of asthma for a delivery system that enables a continued, controlled release of NO over a sustained period of time.

c. Cystic Fibrosis (CF)

Cystic fibrosis is the most common life-limiting autosomal recessive (genetic condition) in people of European ancestry, with up to 1 in 2,500 being affected (WHO, Monogenic diseases—cystic fibrosis). In CF, the lungs, the pancreas, liver, kidneys and intestines become clogged with a sticky mucus. Symptoms usually start in early childhood, and include a persistent cough, frequent chest and lung infections and often poor weight gain.

There is no cure for cystic fibrosis, only interventions aimed at managing the symptoms. As a chronic illness affecting both the respiratory and digestive tract, CF has a significant impact on the quality of life (QoL) in patients if it is not successfully managed. QoL has improved significantly in recent years with better treatments and wider access to healthcare, but average survival still remains around 40 years (Cystic Fibrosis Trust, 2012). Current interventions include mucolytics, bronchodilators, steroids and antibiotics, with the different purposes of loosening mucus, expanding airways, decreasing inflammations and fighting lung infections. In some cases, lung transplantation is carried out.

Several studies have pointed to the potential benefits of Nitric Oxide (NO) in the treatment of multiple symptoms and vulnerabilities of cystic fibrosis patients (Kelley et al., 1998). As well as its bronchiodilatory properties, NO is known to play a part in the movement of cilia in the lung (Rubinstein et al., 1993), in improving ion transport across cell membranes (Beckman et al., 1996), as an effective antimicrobial agent (Fang, 1997) (especially in the killing of bacterial infections such as *P. aeruginosa*) and in decreasing viral replication. All of these aspects could assist in improving management of the different symptoms of CF, impacting on QoL and longevity for patients.

In late 2013 the FDA gave 'orphan drug' designation to a formulation of inhaled nitric oxide gas being developed by Novoteris for treatment of cystic fibrosis. Again, there exists a need to provide a targeted, sustained and precisely dosed release of NO to the patient through a simple inhalation therapy.

d. Chlorine Inhalation (Poisoning)

In most settings, chlorine gas poisoning tends to be mild and due to long-term, low level exposure in the workplace or other setting. However, acute exposure can occur as a result of industrial spills, disasters or in chemical conflict/terrorism scenarios, and can cause asphyxia with respiratory failure, pulmonary edema, acute pulmonary hypertension, cardiomegaly, pulmonary vascular congestion, acute burns of the upper and proximal lower airways, and death. In the modern world, chlorine represents a persistent hazardous material (HAZMAT) threat. Intentional chlorine gas release is included as one of the US Department of Homeland Security 15 'National Planning Scenarios', with projections of up to 17,000 fatalities and 100,000 injuries if it occurs in a densely populated area (Van Sickle et al., 2009). This could quickly overwhelm available treatment facilities.

After chlorine gas exposure, local irritation from hypochlorus and hydrochloric acid results in an inflammatory response of the upper and lower airways, leading to bronchospasm, cough and dyspnea. The acids then produce oxygen free radicals, and disrupt cell membranes and proteins, resulting in the death of alveolar cells and endothelial cells in the adjacent capillaries.

Histologic findings include bronchial edema, desquamation of epithelial cells, erosions and localised necrosis.

There is presently no specific antidote for chlorine inhalation, though several studies have suggested that inhaled or parenteral steroids are effective in decreasing respiratory complications after chlorine exposure (Gunnarsson et al., 2004). More recently, studies have suggested a promising role for Nitric Oxide in preventing chlorine gas toxicity post-exposure (Honavar et al., 2014) and for Nitrite in decreasing lung injury and mortality after inhalation of both chlorine and bromine post exposure. This, along with the vaso-dilating, bronchio-dilating and other properties of NO, make it a promising therapeutic option post chlorine inhalation. Again, there exists however a need for a delivery mechanism that can administer a sustained dose of NO or Nitrite.

e. Influenza

Influenza is an acute respiratory illness due to infection with the influenza virus. There are three serotypes of this virus, each with a number of subtypes. Minor mutations in one or both surface antigens causes seasonal epidemics, where people have only partial immunity from previous exposure. There is also growing evidence that humans can serve as a 'mixing vessel' for some of the 15 types of avian flu subtypes circulating in the bird populations.

Up to 15% of the population can be affected by influenza in any one season, most of these mildly. However the effects of a major pandemic can be devastating. There have been 4 major influenza pandemics in the last 100 years: the one in 1918 killed more than 21 million people; the latest, the swine flu of 2009 affected 209 countries worldwide. In a normal year, 3 to 5 million cases of severe influenza occur, with between 250,000 and 500,000 deaths.

In influenza type A, antiviral drugs amantadine and rimantadine have found to be effective through their action on inhibiting a viral ion channel (M2 protein), thus inhibiting virus replication. However the M2 drug target is not present in other viral strains. However, studies using gaseous Nitric Oxide have demonstrated its effectiveness in vitro and in small animal models to be highly effective in inhibiting infectivity in different strains of influenza types A and B (Regev-Shoshani et al., 2013, Rimelzwaan et al, 1999). This, along with the respiratory and other benefits demonstrated by NO therapy make it an attractive option for therapeutic use in people affected by both mild and more severe influenza. However, there exists a need for a delivery mechanism that can provide a controlled, sustained release of NO.

f. Acute Myocardial Infarction (MI)

Acute Myocardial Infarction (AMI) is caused when blood circulation is acutely cut off from the heart, causing damage to the heart muscle. The mechanism often involves the rupture of an atherosclerotic plaque leading to complete blockage of a coronary artery. Worldwide, around 3 million people have an ST elevation MI every year (STEMI), and a further 4 million have a non-ST elevation MI. The risk of death from STEMI in the developed world is around 10%.

The most effective means of treating AMI is by early revascularization using Thrombolysis or via primary angioplasty (PPCI) to open the epicardial coronary artery and limit the size of the infarct. The latter is the main determinant of outcome. However, following successful opening of the artery, up to 20% of patients continue to deteriorate, due to the 'no reflow' phenomenon, thought to be caused by vasospasm or clotting of the micro-circulation. Aside from its action as a vasodilator, in the right concentrations, NO has also been shown to preserve ischemic blood flow, and to attenuate platelet aggregation and neutrophil-endothelial interaction following ischemia and reperfusion (Schulz et al., 2004). Sustained NO delivery could therefore be of significant benefit to patients affected by the 'no reflow' phenomenon. Finally, in areas of the world where PPCI is not available, a simple delivery mechanism for sustained NO delivery could be used to limit infarct size in the first place, thus improving patient outcomes (Bolli, 2001). Thus, there exists a need for a simple delivery mechanism that can administer a sustained dose of NO.

g. Heart Failure

The prevalence of heart failure worldwide has doubled over the last 25 years, and now stands at 86 million individuals affected worldwide. In the US alone, it causes 300,000 deaths per annum and over 1 million hospitalizations, placing a US$31 billion burden on the national health care budget (Heindenreich, 2013). This is likely to double again in the next 15 years.

A variety of lifestyle, pharmacological, cell or gene based, device based and surgical strategies (sometimes combined) are utilised with Heart Failure patients, depending on disease stage and other factors. However, despite ongoing advances in therapeutic development resulting in some modest survival gains, prognosis remains poor, with 75% of patients in the UK dying within 5 years of first hospital admission (Stewart et al, 2003).

Sustained delivery of NO can be beneficial in Heart Failure through its effect on enhancing myocardial blood flow. More importantly, it has also been shown to have a direct effect on myocardial cells themselves, by stimulating the cyclic GMP pathways, and influencing mitochondrial bioenergetics. The challenge is to provide a sustained, efficient and controlled delivery of NO.

It is therefore an object of the invention to address the needs or shortcomings of the prior art, and preferably to provide a simple means by which a controlled, sustained and targeted dose of NO and/or nitrite can be delivered to a patient.

BRIEF SUMMARY OF THE INVENTION

According to a first aspect of the present invention, there is provided a pharmaceutical formulation comprising either polymeric nanoparticles or polymeric nanoparticles encapsulated within cross-linked polymeric microparticles, wherein the polymeric nanoparticles carry a therapeutic agent suitable for treatment of a disorder loaded within them, for use in the treatment of the disorder, wherein the disorder is selected from chronic obstructive pulmonary disease, bronchial asthma, cystic fibrosis, chlorine inhalation, influenza, acute myocardial infarction and heart failure.

By "nanoparticle" is meant a composition having a mean particle size (preferably diameter) of less than 600 nm, preferably less than 500 nm. Preferably the mean diameter ranges from 1 to 500 nm, more preferably 10-250 nm. In preferred embodiments, the mean diameter is less than 250 nm, preferably less than 200 nm.

By "microparticle" is meant a composition having a mean particle size (preferably diameter) ranging from 0.75 to 10 µm. Preferred mean particle size ranges include 0.75 to 7.5 µm, 1 to 5 µm, 2 to 4 µm. Most preferred range is 1 to 5 µm.

The mean particle size may be determined by any suitable method practiced in the art; examples of suitable methods are exemplified herein.

The nanoparticle plus microparticle formulation described herein may be referred to as a nano-micro-carrier, or nano-micro-particles, or nano-micro formulation.

The present formulations provide therapeutic routes for treatment of chronic obstructive pulmonary disease, bronchial asthma, cystic fibrosis, chlorine inhalation, influenza, acute myocardial infarction and heart failure which are simpler to administer than existing treatments. This is achieved by incorporating a therapeutic agent into nanoparticles.

However, nanoparticles themselves are difficult to administer by inhalation, so these are then incorporated into cross-linked polymeric microparticles. This makes the formulation suitable for dry powder inhalation. The nanoparticles encapsulate and stabilise the drug, while also allowing for pulmonary delivery due to their size. The microparticles can help to make the physical form more suitable for one or another administration route, while also permitting sustained release of the nanoparticles.

The nanoparticles and microparticles are preferably biodegradable, and are preferably biocompatible. By biodegradable is meant that the particles will break down naturally within the body under physiological conditions; preferably the conditions as found within the lung. By biocompatible is meant that the particles will not elicit an immune response from the patient. The nanoparticles preferably biodegrade under physiological conditions to give a therapeutic agent release rate of 0.1-0.3 w % per hour.

The polymeric nanoparticles preferably comprise a chitosan or a chitosan-derivative polymer. Suitable chitosan-derivative polymers include chitosan-PEG, N-trimethyl chitosan, and/or chitosan derivatives having hydrophobic side chains (for example, stearic acid, cholanic acid, phthaloyl, butyl acrylate). Alternatively, the nanoparticles may comprise a copolymer, preferably an amphiphilic copolymer, for example, poly (lactic-co-glycolic acid) (PLGA). In preferred embodiments, the nanoparticles are graft and block copolymers. In one embodiment the nanoparticles comprise PEG-grafted-medium molecular weight N-phythaloyl chitosan (PEG-g-NPhCs), PEG-grafted-medium molecular weight chitosan (PEG-g-MMWCs) or PEG-grafted-oligochitosan (PEG-grafted-OCs). Chitosan or chitosan derivatives are particularly preferred, due to chitosan's ability to enhance absorption in lung tissues through opening the intercellular tight junctions of the lung epithelium. We refer to this ability herein as "epithelial targeting", and this feature also makes similar formulations suitable for administration to other epithelial tissues, for example, the intestine. Thus, in preferred embodiments, the nanoparticles are epithelially targeted.

The polymeric nanoparticles in preferred embodiments have a moisture content, in the dry formulation, of less than 2%.

The polymeric nanoparticles may be produced via emulsion polymerization, ionotropic gelation, polyelectrolyte complexation, and/or self-assembly. In preferred embodiments, the nanoparticles may be produced via self-assembly following sonication of amphiphilic polymer solutions. In an alternative embodiment, the nanoparticles may be produced via self-assembly without sonication to form polymersomes.

In one embodiment, the nanoparticles comprise or consist of a hydrophobic core and a coating shell. In one embodiment, the hydrophobic core comprises magnetically responsive particles, including superparamagnetic iron oxide nanoparticles (SPIONs). In one embodiment, the hydrophobic core is a polymeric core and more, preferably is catioinic, as described herein.

In one embodiment, the hydrophobic core is smart pH-responsive or comprises a smart pH-responsive carrier. Such a feature preferably allows the intracellular release of the therapeutic agent.

In one embodiment, the coating shell comprises cross-linked polymers as described herein. Preferably said polymers are swellable as also described herein.

The cross-linked polymeric microparticles preferably comprise cross-linked hydrogel polymers, and are preferably cross-linked hydrogel microparticles. These may be in the form of semi-interpenetrating polymeric networks (semi-IPNs) and full-IPNs. These semi- and full-IPNs are preferably based on natural polymers such as, but not limited to, chitosan and water soluble chitosan derivatives (such as carboxymethyl and PEGylated derivatives) in a combination with one or more of nontoxic, biocompatible, and biodegradable polymers including, but not limited to, hyaluronate, carrageenan and oligoguluronate. In some embodiments, only chitosan or chitosan derivatives are used. The semi-IPN and IPN microparticles are cross-linked through any suitable method, including ionotropic gelation, polyelectrolyte complexation and/or H-bonding. The nanoparticles-microparticles formulations may be produced using a spray-drying technique, spray gelation, or ionotropic gelation followed by lyophilization. Spray drying is preferred.

The microparticles are preferably swellable; more preferably the microparticles are hydrogel microparticles and the hydrogel is swellable. This allows the hydrogel to absorb moisture from the lung or other delivery site and so permit release of the nanoparticles. The hydrogel is preferably able to swell to at least 200, 300, 400, 500% of the original (dry formulation) size. In a preferred embodiment, a microparticle of 2-5 µm dry diameter is able to swell to at least 20 µm diameter. The microparticle is preferably able to swell to the larger diameter within 10, 9, 8, 7, 6, 5, 4, 3, or 2 minutes from administration to the lungs of a patient. In a further preferred embodiment, the microparticle is able to swell to at least 10 times the dry size within 3 minutes from administration.

The hydrogel preferably comprises less than 10%, preferably less than 7.5%, more preferably less than 5, 4, 3, 2% water when in the dry formulation. In preferred embodiments, this is less than 2%.

The particles preferably biodegrade under physiological conditions (3-5% weight loss per day) to give a drug release rate of less than 1% per hour, more preferably less than 0.5% per hour. In preferred embodiments, the drug release rate is 0.1-0.3 w % per hour.

The microparticles may comprise a pH responsive carrier. Smart pH-responsive particles for drug delivery are known, and are used in situations where it is desirable to release a drug from a carrier under certain pH conditions; for example, when the carrier is in a specific environment, such as the intestine. Examples of the preparation and use of pH-responsive carriers are given in PS Stayton and A S Hoffman, "Smart pH-responsive carriers for intracellular delivery of biomolecular drugs", in V Torchilin (ed), Multifunctional Pharmaceutical Nanocarriers, Springer Science and Business Media, 2008; and in Stephanie J. Grainger and Mohamed E. H. El-Sayed, "STIMULI-SENSITIVE PARTICLES FOR DRUG DELIVERY", in Biologically Responsive Hybrid Biomaterials, Esmaiel Jabbari and Ali Khademhosseini (Ed), Artech House, Boston, Mass., USA.

In preferred embodiments, the therapeutic agent is at least one Nitric Oxide (NO) donor and/or at least one Nitrite donor. Preferably, the therapeutic agent is a NO donor and/or a Nitrite donor. In one embodiment, the NO donor is selected from organic nitrates, nitrite salts, S-Nitrosoglutathione (GSNO) and S-Nitrosothiols. In a preferred embodiment, the NO donor is sodium nitrite. In another embodiment, the nitrite donor is inorganic nitrite salt selected from, but not limited to, sodium nitrite and potassium nitrite The dosage of the therapeutic agent may be selected depending on the desired administration dose to the patient, and may vary depending on the agent to be used, and the composition of the nano and microparticles.

According to a further aspect of the invention, there is provided a composition comprising polymeric nanoparticles or polymeric nanoparticles encapsulated within cross-linked polymeric microparticles, wherein the polymeric nanoparticles carry a therapeutic agent suitable for treatment of chronic obstructive pulmonary disease, bronchial asthma, cystic fibrosis, chlorine inhalation, influenza, acute myocardial infarction or heart failure loaded within them. The invention also provides the use of a composition comprising polymeric nanoparticles encapsulated within cross-linked polymeric microparticles, wherein the polymeric nanoparticles carry a therapeutic agent suitable for treatment of chronic obstructive pulmonary disease, bronchial asthma, cystic fibrosis, chlorine inhalation, influenza, acute myocardial infarction and heart failure loaded within them in the manufacture of a medicament for the treatment of the above mentioned conditions.

A further aspect of the invention provides a method of treatment of a disorder selected from, chronic obstructive pulmonary disease, bronchial asthma, cystic fibrosis, chlorine inhalation, influenza, acute myocardial infarction and heart failure, the method comprising administering a composition comprising polymeric nanoparticles or polymeric nanoparticles encapsulated within cross-linked polymeric microparticles, wherein the polymeric nanoparticles carry a therapeutic agent suitable for treatment of the above disorders loaded within them to a patient in need thereof, wherein the composition is administered by inhalation.

A further aspect of the invention provides a pharmaceutical formulation comprising polymeric nanoparticles encapsulated within smart pH-responsive cross-linked polymeric microparticles, wherein the polymeric nanoparticles carry a therapeutic agent suitable for treatment of chronic obstructive pulmonary disease, bronchial asthma, cystic fibrosis, chlorine inhalation, influenza, acute myocardial infarction or heart failure loaded within them, wherein the pH-responsive microparticles are targeted to the intestine, and wherein the nanoparticles are targeted to the epithelium. This aspect of the invention may be suitable for intestinal or oral administration, for example. Smart pH-responsive particles for drug delivery are known, and are used in situations where it is desirable to release a drug from a carrier under certain pH conditions; for example, when the carrier is in a specific environment, such as the intestine. Examples of the preparation and use of pH-responsive carriers are given in P S Stayton and A S Hoffman, "Smart pH-responsive carriers for intracellular delivery of biomolecular drugs", in V Torchilin (ed), Multifunctional Pharmaceutical Nanocarriers, Springer Science and Business Media, 2008; and in Stephanie J. Grainger and Mohamed E. H. El-Sayed, "STIMULI-SENSITIVE PARTICLES FOR DRUG DELIVERY", in Biologically Responsive Hybrid Biomaterials, Esmaiel Jabbari and Ali Khademhosseini (Ed), Artech House, Boston, Mass., USA.

A yet further aspect of the invention provides an injectable pharmaceutical formulation comprising polymeric nanoparticles carrying a therapeutic agent suitable for treatment of chronic obstructive pulmonary disease, bronchial asthma, cystic fibrosis, chlorine inhalation, influenza, acute myocardial infarction or heart failure loaded within them, and wherein the nanoparticles are targeted to the epithelium. Preferably the therapeutic agent is a NO donor. For injectable formulations, it may not be beneficial to provide microparticles, and the nanoparticles may be injected directly. Such formulations may find application where inhalation is not practical for one reason or another, or where sites other than the lungs are to be targeted.

In a final aspect of the invention there is provided an oral or inhalable formulation comprising polymeric nanoparticles, polymeric microparticles, or polymeric nanoparticles encapsulated within smart pH-responsive cross-linked polymeric microparticles, wherein the polymeric nanoparticles carry Nitric Oxide and/or a Nitrite donor loaded within them, and wherein the pH-responsive microparticles are targeted to the intestine.

BRIEF DESCRIPTION OF THE DRAWINGS

FIGS. 3(a), 3(b), 3(c) and 3(d) show characterization and NO release profile from NO nanoparticles.

DETAILED DESCRIPTION OF THE INVENTION

Figure 1:
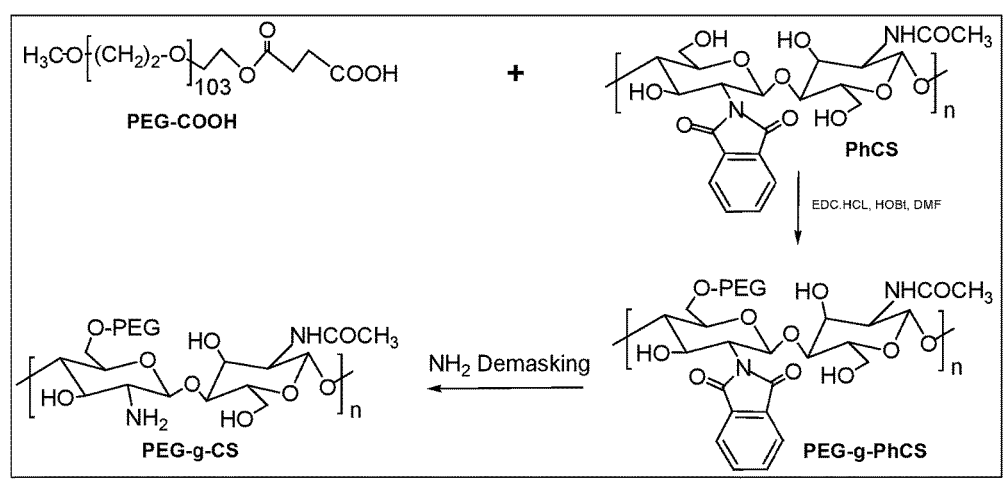
FIG. 1 shows synthesis of PEG-CS copolymers.

The present invention provides novel formulations of therapeutics for the treatment of a disorder selected from chronic obstructive pulmonary disease, bronchial asthma, cystic fibrosis, chlorine inhalation, influenza, acute myocardial infarction and heart failure, through the use of NO and/or nitrite donors as the principle therapeutic agents. The agents are incorporated into biodegradable polymeric nanoparticles, which themselves are incorporated into hydrogel microparticles or smart pH-responsive microparticles.

Background art which may be of benefit in understanding the invention includes:

Beckman J, Koppenol W. Nitric oxide, superoxide and peroxynitrite: the good, the bad and the ugly. American Journal of Physiology—Cell Physiology, 1996; 271(5): 1424-1437

Bolli R. Cardioprotective function of inducible nitric oxide synthase and role of nitric oxide in myocardial ischemia and preconditioning: an overview of a decade of research. J Mol Cell Cardiol 2001; 33:1897-918 Cystic Fibrosis Trust (UK). UK Cystic Fibrosis Registry, Annual Data Report 2012.

Du, J. El-Sherbiny, I. M. & Smyth, H. D. C. (2014). Swellable ciprofloxacin-loaded nano-in-micro hydrogel particles for local drug delivery. AAPS PharmSciTech, 15(6):1535-44.

Dupuy P, Shore S, Drazen J, Frostell C, Hill W, Zapol W. Bronchiodilator action of inhaled Nitric Oxide in Guinea Pigs. J Clin Inv; Volume 90, August 1992:421-428

El-Sherbiny, I. M., & Smyth, H. D. C. (2012). Controlled release pulmonary administration of curcumin using swellable biocompatible nano-microparticles systems. Molecular Pharmaceutics, 9(2), 269-280.

El-Sherbiny I M, and Smyth, H D C. (2010) Biodegradable nano-micro carrier systems for sustained pulmonary drug delivery: (I) self-assembled nanoparticles encapsulated in respirable/swellable semi-IPN microspheres. Int J. Pharm 395: 132-141.

El-Sherbiny I M, Mcgill S, and Smyth H D C. (2010) Swellable microparticles as carriers for sustained pulmonary drug delivery. J. Pharm Sci, 99(5): 2343-2356.

El-Sherbiny I M, and Smyth H D C. (2010) Novel cryomilled physically cross-linked biodegradable hydrogel microparticles as carriers for inhalation therapy. J. Microencapsulation, 27(7): 561-572.

El-Sherbiny I M, Abdel-Mogibb M, Dawidar A, Elsayed A, and Smyth H D C. (2010) Biodegradable pH-responsive alginate-poly (lactic-co-glycolic acid) nano/micro hydrogel matrices for oral delivery of silymarin, CarbohydrPolym, 83, 1345-1354.

El-Sherbiny I M, and Smyth H D C. (2010) PLGA nanoparticles encapsulated in respirable/swellable hydrogel microspheres as potential carriers for sustained drug delivery to the lung. Annual Meeting of American Association of Pharmaceutical Scientists, New Orleans, La.

El-Sherbiny I M, and Smyth H D C. (2010) Nano-micro carrier systems for sustained pulmonary drug delivery. Biomedical Engineering Society Annual Meeting (BMES), Austin, Tex.

Selvam P, El-Sherbiny I M, and Smyth H D C. (2010) Swellable microparticles for sustained release drug delivery to the lung using propellant driven metered dose inhalers. Biomedical Engineering Society Annual Meeting (BMES), Austin, Tex.

El-Sherbiny I M, and Smyth H D C. (2010) Novel non-covalently cross-linked hydrogel nano-microparticles for inhalation therapy. Annual Meeting of American Association of Pharmaceutical Scientists, New Orleans, La.

El-Sherbiny I M, and Smyth H D C. (2009) Cryomilled physically cross-linked biodegradable hydrogel microparticles as novel potential carriers for inhalation therapy. Annual Meeting of American Association of Pharmaceutical Scientists, Los Angeles, Calif., AM-09-01692.

El-Sherbiny I M, and Smyth H D C. (2009) Novel spray dried biodegradable semi-IPN hydrogel microspheres for pulmonary drug delivery. Annual Meeting of American Association of Pharmaceutical Scientists, Los Angeles, Calif., (AM-09-01708).

Fang F. Mechanisms of Nitric Oxide related antimicrobial activity. J Clin Inv, June 1997; Vol 99(12):2818-2825

Gaston B, Reilly J, Drazen J, Fackler J, Ramdev P, Arnelle D, Mullins M, Sugarbaker D, Chee C, Singel D. Endogenous nitrogen oxides and bronchiodilator S-nitrosothiols in human airways. PNAS, Dec. 1, 1993; Vol 90 (No 23): 10957-10961

Gunnarsson M, Walther S M, Seidal T et al. The effects of inhalation of corticosteroids immediately after experimental chlorine gas lung injury. J Trauma, 200; 48:101-7

Heindenreich P et al. Forecasting the impact of heart failure in the United States: a policy statement from the American Heart Association. Circ Heart Fail 2013 May; 6(3): 606-19

Honavar J, Doran S, Joo-Yeun O L, Steele C, Matalon S, Patel R. Nitrite Therapy improves survival postexposure to chlorine gas. Am J Phisiol, December 2014; Vol 307: No 11, L888-L894

Kelley T, Drumm M. Inducible nitric oxide synthase expression is reduced in cystic fibrosis murine and human airway epithelial cells. J Clin Invest 1998 Sep. 15; 102(6): 1200-1207

Meurs H, Maarsingh H, Zaagsma J. Arginase and asthma: novel insights into nitric oxide homeostasis and airway hyperresponsiveness. Trends in Pharmacological Sciences. September 2003; Vol 24(9): 450-455

Regev-Shoshani G, Vimalanathan S, McMullin B, Road J, Av-Gay Y, Miller C. Gaseous nitric oxide reduces influenza infectivity in vitro. Nitric Oxide, May 2013; Vol 31: 48-53

Rimelzwaan G F, Baars M M, Osterhaus A D. Inhibition of Influenza Virus Replication by Nitric Oxide. J Virol 1999 October; 73(10):8880-8883

Rubinstein J, Robbins R, Leise K, Sisson J. Modulation of airway epithelial cell ciliary beat frequency by Nitric Oxide. Biochemical & Biophysical Research Communications, 26 Feb. 1993; Vol 191(1): 83-88

Schulz R, Kelm M, Heusch G. Nitric Oxide in myocardial ischemia/reperfusion injury. Cardiovascular Research 61 (2004): 402-413

Stewart S, Macintyre K, Capewell S et al. Heart Failure and the ageing population: an increasing burden in the $21^{st}$ century? Heart 2003 January: 89(1): 49-53

Van Sickle D, Wenk M A, Belflower A et al. Acute health effects after exposure to chlorine gas released after a train derailment. Am J Emerg Med 2009; 27:1-7

World Health Organization (who.int). Burden of COPD

World Health Organization (who.int). Monogenic diseases-cystic fibrosis.

Reference to these publications should not be taken as an admission that the contents of any particular document are relevant prior art. However, the skilled person is referred to each of these publications for details of ways in which nanoparticles and/or microparticles may be produced.

Various preliminary studies (referred to in the citations listed above) performed with regard to options for inhalation, and oral therapy support the proposal that polymeric nanoparticles and/or nanoparticles-microparticles carrier systems will improve bioavailability, increase targeting, reduce dose frequency, avoid macrophage clearance and confer sustained delivery of therapeutic agents to the lung compared to free drugs. Remarkably, the preliminary data has shown that:

(1) The loading of therapeutic agents into polymeric nanoparticles has the potential to significantly enhance dissolution and absorption, and consequently can improve the bioavailability of the loaded therapeutic agent.

(2) NO donor-loaded nanoparticles can be incorporated into novel cross-linked microparticles with physicochemical characteristics (aerodynamic size, shape, moisture content, etc) appropriate for inhalation therapy.

(3) the design and composition of the nanoparticles-microparticles carriers can be modulated to allow them to absorb moisture and expand rapidly to evade endocytosis by macrophage cells.

(4) biodegradation rates of the developed carriers are controllable.

(5) the polymeric nanoparticles-microparticles systems can be used efficiently for dry powder inhalation therapy.

(6) cross-linked polymeric microparticles incorporating drug-loaded nanoparticles can efficiently confer sustained release of these drugs once deposited in the lung.

Hypothesis

The hypothesis underlying this invention is that the development of appropriate respirable cross-linked polymeric nano or nano-microparticle systems will enhance bioavailability, increase deep lung targeting, reduce dose frequency, avoid macrophage clearance and confer sustained pulmonary delivery of Nitric Oxide and/or Nitrite for the treatment of chronic obstructive pulmonary disease, bronchial asthma, cystic fibrosis, chlorine inhalation, influenza, acute myocardial infarction or heart failure, compared to free drugs and other existing therapies. Also, that the formulation of the above into pre-designed biodegradable and biocompatible smart pH-responsive hydrogel particles will improve bioavailability, reduce dose frequency, increase targeting, and confer sustained oral and intravascular delivery of these interventions compared to free drugs and other existing therapies.

1. Composition of Nanoparticles

Our preliminary studies showed that incorporation of NO and/or Nitrite donor-loaded nanoparticles into respirable cross-linked microparticles can allow for additional control of Nitric Oxide action and release. Also, in our preliminary investigations, we found that loading of hydrophobic active ingredients into nanoparticles (made of ubiquitous polymers such as PLGA) considerably enhances the dissolution/absorption of these ingredients. Building on these observations, a new series of specifically designed polymeric nanoparticles were obtained via self assembly of a new series of amphiphilic graft and block copolymers. The developed graft and block copolymers are based on natural polymers and chemically modified natural polymers such as, but not limited to, chitosan, chitosan derivatives, alginate, carrageenan, and cellulose derivatives.

Materials: The amphiphilic copolymers were produced via chemical modifications of some natural polymers such as, but not limited to, chitosan and chitosan derivatives through introducing of hydrophilic side chains (such as PEG) and/or hydrophobic moieties (mainly, stearic acid, cholanic acid, phthaloyl, and butyl acrylate). Chitosan, a cationic biopolymer obtained through alkaline N-deacetylation of chitin, has been selected as a preferred base polymer for the development of the nanoparticles due to its numerous desirable characteristics including biodegradability, non-toxicity, biocompatibility, in addition to its ability to enhance therapeutic agent absorption in lung tissues through opening the intercellular tight junctions of the lung epithelium (see Parka J H, Kwon S, Lee M, Chung H, Kim J H, Kim Y S, Park R W, Kim I S, Seo S B, Kwon I C, and Jeong S Y. (2006) Self-assembled nanoparticles based on glycol chitosan bearing hydrophobic moieties as carriers for doxorubicin: in vivo biodistribution and anti-tumour activity. Biomaterials, 27: 119-126).

Preparation Method: The self-assembled polymeric nanoparticles were prepared with (and without) sonication of different concentrations of the modified polymer solutions at different sonication powers (30-75 W) for different intervals. The effect of relative compositions plus the different preparation parameters onto the physicochemical characteristics (mainly particle size) of the resulting nanoparticles were investigated extensively, to ensure desired properties have been achieved.

Therapeutic agent loading: The nanoparticles of different architectures loaded with the bioactive moieties (NO and/or Nitrite donors) were prepared in the same manner used for plain nanoparticles. Then, the effect of relative compositions plus the different preparation parameters onto both therapeutic agent loading capacity and loading efficiency (%) of the produced nanoparticles were studied in detail to determine optimal loading.

2. Nanoparticle Characterization

Polymer Characterization: The synthesized and chemically modified polymers used as pre-cursors for the nanoparticles were characterized using different analytical tools such as elemental analysis, FT-IR, differential scanning calorimetry (DSC), and thermogravimetric analysis (TGA). Also, the crystallography patterns of powdered modified polymers were investigated by X-ray diffraction (XRD).

Physicochemical characterization of the developed nanoparticles: The physicochemical properties of the developed nanoparticles such as particle size, moisture content, and morphology were examined using dynamic light scattering, moisture analyzer, scanning electron, and atomic force microscopy. Also, the biodegradation rates of the nanoparticles were estimated. Both plain and cargo (NO and Nitrite donor)-loaded nanoparticles with optimum physicochemical characteristics, NO donor loading capacity, and NO and Nitrite release patterns were selected for further use in the preparation of a series of novel respirable cross-linked polymeric nano-microparticles carriers.

3. Microparticle Composition

Based on our preliminary studies, the developed nanoparticles must be encapsulated or formulated into microparticles for pulmonary drug delivery due to their small aerodynamic size, which normally leads to limited deposition in the airways and extensive exhalation from the lungs following inspiration. Also, nanoparticles-based carrier systems may aggregate in both dry powder and liquid forms which causes rapid clearance by macrophage cells. This aspect of the invention develops a range of novel carrier systems for controlling therapeutic agent delivery (mainly pulmonary) and combines the benefits of both polymeric nanoparticles and the respirable micron-size cross-linked hydrogel particles.

Materials: The respirable microparticles developed comprise of semi-interpenetrating polymeric networks (semi-IPNs) and full-IPNs. These semi- and full-IPNs are based mostly on natural polymers such as, but not limited to, chitosan and water soluble chitosan derivatives (such as carboxymethyl and PEGylated derivatives) in a combination with one or more of nontoxic, biocompatible, and biodegradable polymers including, but not limited to, hyaluronate, carrageenan and oligoguluronate. The semi-IPN and IPN microparticles are cross-linked through ionotropic gelation, polyelectrolyte complexation and/or H-bonding. These microparticles incorporating NO donor-loaded nanoparticles were produced using spray-drying technique, spray gelation, and ionotropic gelation followed by lyophilization.

4. Nano-Microparticle Characterization

The design criteria of the nano-microparticle carriers requires geometric and aerodynamic particle sizes for lung delivery (1-5 µm aerodynamic diameter of dry particles), rapid dynamic swelling (>20 µm within minutes), appropriate morphology, reasonable biodegradation rates, low moisture content, high NO and/or Nitrite donor loading efficiency and desirable Nitric Oxide and Nitrite release profiles.

The physicochemical properties of the nano-microparticles carriers, such as particle size, moisture content, and morphology were investigated with the aid of dynamic light scattering (DLS), moisture balance, scanning electron microscopy (SEM), and atomic force microscopy (AFM). Particle density and dynamic swelling were determined using pycnometer and laser diffraction, respectively. The loading capacity, and release kinetics of the incorporated NO donors were determined. Also, the biodegradation rates of the developed formulations were measured. Based on the pre-suggested design criteria, the NO donor-loaded nano-microparticles carriers with optimum physicochemical characteristics, high NO donor loading efficiency, and desirable in vitro Nitric Oxide and Nitrite release kinetics will be selected and optimized for further in vitro assessment of their delivery performance. Further selection and optimization of the nano-micro carriers will then determine efficacy in the treatment of chronic obstructive pulmonary disease, bronchial asthma, cystic fibrosis, chlorine inhalation, influenza, acute myocardial infarction and heart failure in an in vivo (rat or mouse) model, before further development towards human trials.

Characteristics and Potential Uses

Improving the physicochemical characteristics of Nitric Oxide and Nitrite donors via appropriate formulation and targeting would enhance its overall target organ bioavailability.

Incorporation of Nitric Oxide and Nitrite donors suitable for treatment of chronic obstructive pulmonary disease, bronchial asthma, cystic fibrosis, chlorine inhalation, influenza, acute myocardial infarction and heart failure in polymeric nano-micro-carriers is advantageous over other carriers because of stability, potential for improved permeability across the physiological barriers, increased bioavailability and also reduction of undesirable side effects. In addition, the polymeric nano-micro-carriers can be designed with desirable physicochemical characteristics via the selection of appropriate candidates from a wide range of the available natural and synthetic polymers.

EXAMPLES (I) Preparation of Plain and Therapeutic Agent-Loaded Poly (Lactic-Co-Glycolic Acid) Nanoparticles The plain and therapeutic agents-loaded poly (lactic-co-glycolic acid) [PLGA] nanoparticles were prepared using "single Emulsion/solvent evaporation technique" through a procedure similar to that described in our previous work (see El-Sherbiny I M et al, 2010, Carbohydr Polym, 83, 1345-1354). Briefly, 1 g of PLGA was dissolved in 50 ml of methylene dichloride. Then, to this PLGA solution, the therapeutic agent (NO donor) solution was added with stirring. A 2.5% w/v aqueous polyvinyl alcohol (PVA) solution (70 ml) was prepared to which, the PLGA/therapeutic agent mixture was added dropwise while vortexing the capping agent (PVA) solution at high setting. The mixture was then sonicated for 2 min at 50% amplitude to create an oil-in-water emulsion. The sonication process was repeated three times until the desired size of the nanoparticles was obtained. The sonication process was performed in an ice-water bath with using pulse function (10 s pulse on, and 10 s pulse off) in order to evade the heat built-up of the PLGA/therapeutic agent solution during the sonication. Afterwards, the emulsion was immediately poured into 100 ml of an aqueous 0.3% w/v PVA solution with rapid stirring. The resulting PLGA nano-emulsion was stirred overnight in uncovered container to allow for methylene chloride and ethanol evaporation. The resulting PLGA NPs aqueous suspension was used directly or further used in the preparation of the nano-in-microparticles for inhalation. The prepared PLGA nanoparticles showed dense, compact, and integrated spherical shapes with particle radius of 233±15 and 280±14 nm for the plain and the drug-loaded PLGA nanoparticles, respectively, as determined by DLS.

(II) Preparation of Plain and Therapeutic Agent-Loaded Chitosan-Based Nanoparticles (1) Preparation of PEG-Grafted-CS Copolymer The copolymer of PEG grafted onto CS was prepared (as illustrated in FIG. 1) by a modified method of that reported in our earlier study (El-Sherbiny, I. M., & Smyth, H. D. C. (2012). Controlled release pulmonary administration of curcumin using swellable biocompatible nano-microparticles systems. Molecular Pharmaceutics, 9(2), 269-280)) and described briefly as follows:

(i) Preparation of PEG-COOH: methoxy-PEG (100 g, 20 mmol), 4-dimethylaminopyridine, DMAP (2.44 g, 20 mmol), triethylamine (2.02 g, 20 mmol), and succinic anhydride (2.4 g, 24 mmol) were dissolved in 300 ml of dry dioxane. The mixture was stirred at room temperature for 2 days under a dry nitrogen atmosphere. Dioxane was then evaporated under vacuum and the residue was taken up in CCl4, filtered and precipitated by diethyl ether to produce PEG-COOH powder. (ii) Masking of the NH2 groups of CS: phthalic anhydride (44.8 g, 5 molequivalent to pyranose rings) was reacted with 10 g of CS in 150 ml of DMF at 130° C. under inert atmosphere for 10 h. The resulting phthaloyl CS (PhCS) was then collected by filtration after precipitation on ice, washed extensively with methanol, and dried at 45° C. under vacuum to produce the yellowish brown PhCS. (iii) Conjugation of PEG-COOH with PhCS: PEG-COOH (37.9 g) was stirred with PhCS (5.0 g, 0.4 mol equivalent to PEG-COOH) in 70 ml of DMF. Then, 1-hydroxybenzotrizole, HOBt (3.4 g, 3 mol equivalent to PEG-COOH) was added with stirring at room temperature until a clear solution was obtained. The 1-ethyl-3-(3-dimethylaminopropyl) carbodiimide hydrochloride, EDC.HCl (4.25 g, 3 mol equivalent to PEG-COOH) was then added with stirring the mixture overnight at room temperature. A purified PEG-g-PhCS copolymer (5.47 g, white product) was obtained after dialysis of reaction mixture against distilled water followed by washing with ethanol. (iv) Demasking of PEG-g-PhCS: PEG-g-PhCS (4.1 g) was heated up to 100° C. with stirring under inert atmosphere in 20 ml of DMF. Then, 15 ml of hydrazine hydrate was added and the reaction was continued for 1.5 h. The resulting PEG-g-Cs was purified by dialysis against a (1:1) mixture of ethanol and deionized water then dried under vacuum at 45° C.

2. Preparation of PEG-CS-Oleic and PEG-CS-Cholanic Acid Copolymers

Figure 2A:
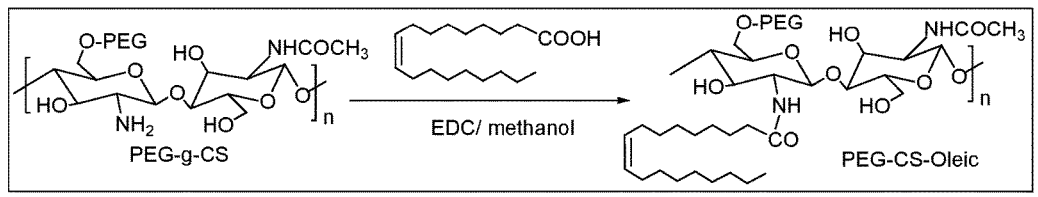
FIGS. 2(a) and 2(b) show synthesis of PEG-CS-oleic and PEG-CS-cholanic copolymers.
Figure 2B:
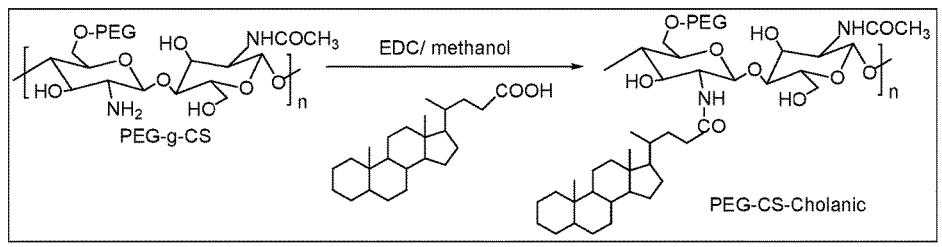

Hydrophobic moieties (HM) including oleic, and cholanic acid were coupled to CS backbone of the PEG-g-CS by formation of amide linkages through the EDC-mediated reaction as follows (FIGS. 2(a) and 2(b)): Briefly, PEG-g-CS (1 g) was dissolved in 0.6% (w/v) aqueous acetic acid solution (100 ml) and diluted with 85 ml methanol. HM was then added to PEG-g-CS solution at 0.4-0.5 mol/l glucosamine residue of CS followed by a drop-wise addition of 15 ml EDC methanol solution (0.07 g/l) while stirring at room temperature. After 20 h, the reaction mixture was added to 200 ml of methanol/ammonia solution (7/3, v/v)

while stirring. The precipitated material was filtered; washed with distilled water, methanol, and ether; and then dried under vacuum for 20 h at room temperature. The DS, which represents the number of HM groups per 100 amino groups of CS, was evaluated using normal titration.

3. Characterization of the Modified Polymers

The synthesized and chemically modified polymers used as pre-cursors for the nanoparticles fabrication were characterized using several analytical techniques such as elemental analysis (EA), Fourier transform infrared (FT-IR), nuclear magnetic resonance (NMR), differential scanning calorimetry (DSC), and thermogravimetric analysis (TGA). Also, the crystallography patterns of powdered modified polymers were investigated by X-ray diffraction (XRD).

4. FT-IR and Elemental Analysis Data of Some of the Developed Polymers and Copolymers PhCS: FT-IR (vmax, cm-1) 3286, 2972, 1770, 1689, 1401, 1050, 727; $(C_8H_{13}NO_5)_{0.2363}(C_6H_{11}NO_4)_{0.016}(C_{14}H_{13}NO_6)_{0.747}$, calculated (%) (DS=0.97) (%): C, 55.71; H, 4.86; N, 5.21. found (%), C, 60.27; H, 4.80; N, 4.97. PEG-COOH: FT-IR (vmax, cm-1) 3502, 2879, 1743, 1114; $(C_{231}H_{461}O_{117})$, calculated (%): C, 54.38; H, 9.04. found (%), C, 56.3; H, 9.21. PEG-PhCS copolymer: FT-IR (vmax, cm-1) 3411, 2901, 1739, 1712, 1091, 720. found EA (%), C, 56.21; H, 4.61; N, 5.22. PEG-CS copolymer: FT-IR (vmax, cm-1) 3305, 2871, 1706, 1099. found EA (%), C, 40.51; H, 4.74; N, 14.09.

5. Development of Plain and NO Donor-Loaded Modified CS-Based Self-Assembled Nanoparticles The developed modified CS copolymers (PEG-g-CS, PEG-CS-Oleic, and PEG-CS-Cholanic) were used to develop a new series of self-assembled nano-carrier systems for the controlled sustained delivery of Nitric Oxide. The nanoparticles were prepared with and without sonication of different concentrations (0.03-3%) of the modified polymers solutions using probe sonicator. The sonication process was performed at different sonication powers (20-45 W) for different intervals (30-180 s). The effect of relative compositions plus the different preparation parameters onto the physicochemical characteristics (particle size, morphology, NO donor loading capacity, and moisture content) of the resulting nanoparticles was investigated. The prepared self-assembled nanoparticles showed particle radius of 65±6 and 115±9 nm for the plain and the NO donor loaded nanoparticles, respectively, as determined by DLS.

6. Development of Plain and NO Donor-Loaded Modified CS-Based Hydrogel Nanoparticles The prepared CS copolymers (PEG-g-CS, PEG-CS-Oleic, and PEG-CS-Cholanic) were used to develop new series of hydrogel nano-carrier systems for the controlled sustained delivery of NO. This has been achieved using various types of crosslinkers (mainly tripolyphosphate, TPP and genipin). The preparation was carried out in a mild aqueous media to ensure the stability of the loaded therapeutic agent (NO-donor). The prepared self-assembled nanoparticles showed particle radius of 295±19 and 311±24 nm for the plain and the NO donor-loaded nanoparticles, respectively, as determined by DLS.

7. Development of Plain and NO Donor-Loaded Respirable Nano-Microparticles

Figures 4A, 4B:
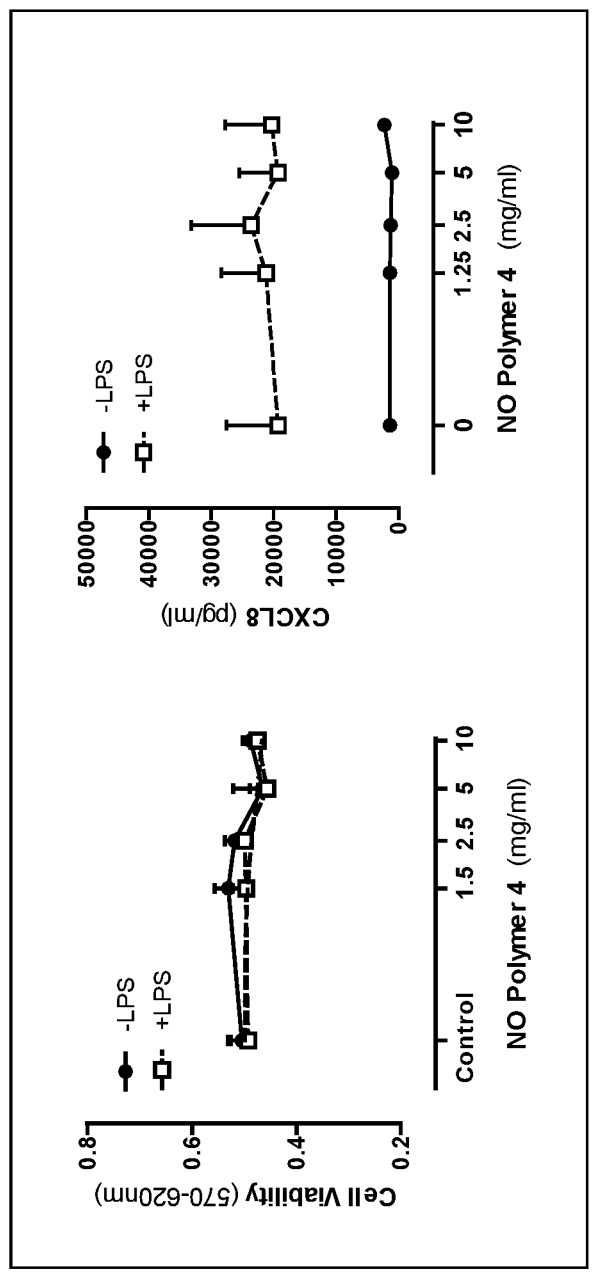
FIGS. 4(a) and 4(b) show the effect of NO nanoparticles on viability and chemokine release from endothelial cells.

The developed PLGA, self-assembled or hydrogel nanoparticles loaded with an NO-donor were incorporated into respirable semi-interpenetrating polymeric networks (semi-IPNs) or full-IPNs microparticles. These semi- and full-IPNs were based mostly onto CS derivatives (such as N-trimethyl CS, carboxymethyl CS, and PEGylated CS) in a combination with one or more of nontoxic, biocompatible, and biodegradable polymers including, sodium alginate, hyaluronate, carrageenan and oligoguluronate. The semi-IPN and IPN microparticles were cross-linked through ionotropic gelation, polyelectrolyte complexation and/or H-bonding. The microparticles incorporating NO donor-loaded nanoparticles were produced using spray gelation, ionotropic gelation followed by lyophilization, or spray-drying technique (NANO-01A nano-spray dryer, MECC CO., LTD., Japan). The developed nano-microparticles powder showed desirable swelling extents (10-24 times of dry size) within three minutes and also showed accepted moisture contents as dry powders (less than 1.6%), good enzymatic degradation rates, promising therapeutic agent loading capacity (more than 90%), and consistent sustained release of Nitric Oxide.

EXPERIMENTS

Nanoparticles were prepared as described above from a combination of polymers including chitosan of low molecular weight, PEG 400 and polyvinyl pyrolidone (PVP), and other materials such as glucose and tetramethyl orthosilicate. Particles were either loaded with an NO donor (referred to as "NO nanoparticles") or not ("control" or "plain" nanoparticles). Glucose was used to perform a thermal reduction of the loaded NO-donor, sodium nitrite (NaNO2) to generate NO gas. The NO remain entrapped inside the nanoparticles powder until undergoing a sustained release because of the swelling of the prepared hydrogel-based nanoparticles upon exposure to moist environment. Various nanoparticles were prepared with different concentrations of the NO-donor, sodium nitrite. In the following experiments, a sample referred to as "NO-Polymer 4" was used. This was prepared as follows: Sodium nitrite solution was prepared (1 g in 30 mM PBS at pH 7.5). Then, D-glucose was added at 40 mg D-glucose/mL of sodium nitrite solution followed by addition of PVP (6.25 mg) with stirring. Afterwards, PEG-400 was added at 0.5 mL PEG/10 mL of solution. Acidic chitosan solution (0.5% w/v) of low molecular weight was then added at a ratio of 0.5 mL/10 mL of sodium nitrite solution. In another container, acidic solution of tetramethyl orthosilicate (2.5 mL/0.6 ml HCl) was prepared and sonicated in ice bath, then added to the NO-donor solution (1 mL tetramethyl orthosilicate/10 mL solution). The resulting mixture was then stirred and set aside for gelation, followed by freeze drying. The control nanoparticles were prepared using the same procedures but without the NO-donor.

The nanoparticles were characterised by powder X-ray diffraction (FIG. 3(*a*)) and themogravimetric analysis (FIG. 3(*b*)). Particles were also assessed for NO release over a period of 8 hours (FIG. 3(*c*)) and NO release over 20 minutes from different concentrations of NO nanoparticles (0.75, 1.25, 2.5, 5, and 10 mg/ml) compared to control plain nanoparticles (at 5 mg/ml). It can be seen that the majority of NO is released in the first 100 or so minutes, while higher concentrations of nanoparticles release more NO.

FIGS. 4(a) and 4(b) show the effect of the NO nanoparticles used in FIGS. 3(a)-3(d) on viability (FIG. 4(a)) and release of the chemokine CXCL8 (FIG. 4(b)) from endothelial cells grown from blood of healthy donors with or without stimulation with LPS. Nanoparticles were contacted with the cells at concentrations of 1.5, 2.5, 5, and 10 mg/ml.

Figures 5A, 5B:
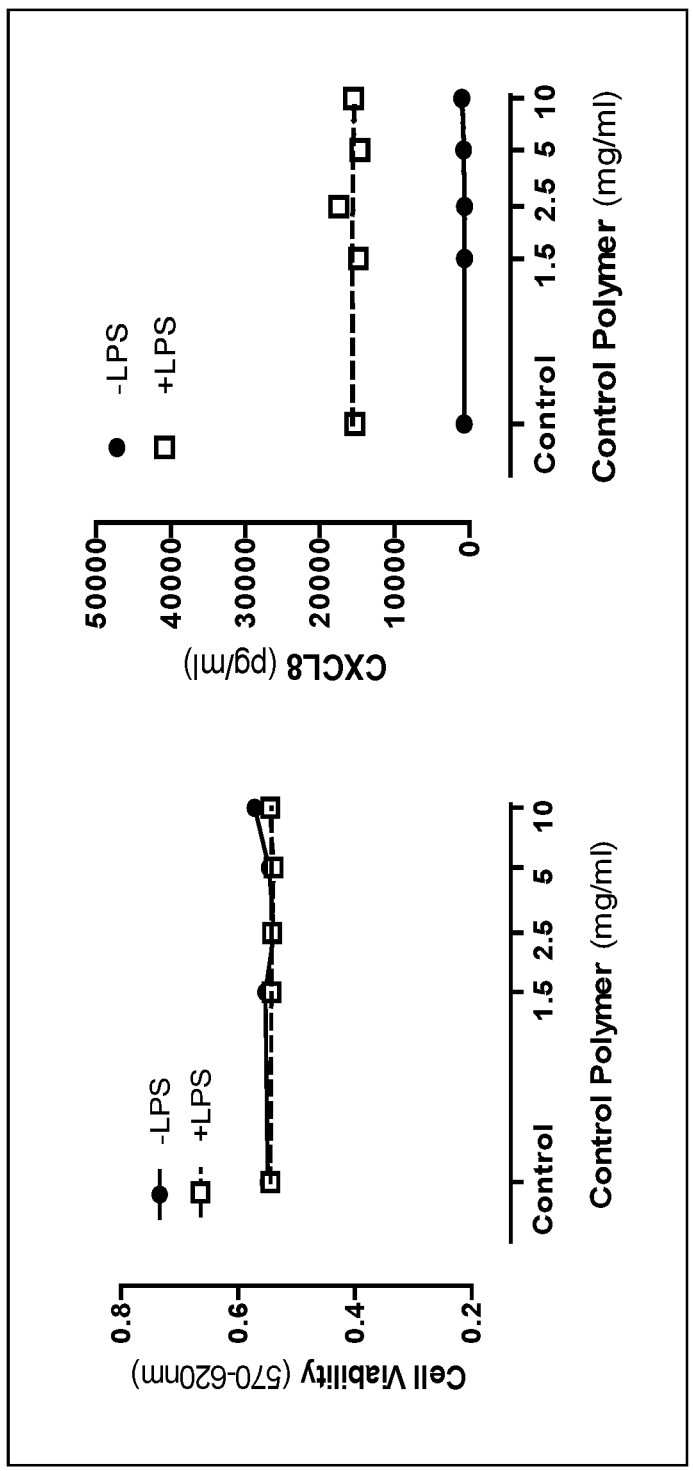
FIGS. 5(a) and 5(b) show the effect of control nanoparticles on viability and chemokine release from endothelial cells.

FIGS. 5(a) and 5(b) show the effect of control nanoparticles on viability (FIG. 5(a)) and release of the chemokine CXCL8 (FIG. 5(b)) from endothelial cells grown from blood of healthy donors with or without stimulation with LPS. Nanoparticles were contacted with the cells at concentrations of 1.5, 2.5, 5, and 10 mg/ml. There is essentially no effect of the nanoparticles lacking NO.

Thus, these experiments demonstrate that NO-releasing agents can be incorporated into nanoparticles, and that these nanoparticles demonstrate significant vasodilatory, bronchiodilatory, smooth muscle relaxant, viral inhibition and antimicrobial properties in in vitro studies and in a mouse model. Sustained NO release has also been shown to preserve ischemic blood flow, and to attenuate platelet aggregation and neutrophil-endothelial interaction following ischemia and reperfusion and to act on myocardial cells themselves, by stimulating the cyclic GMP pathways, and influencing mitochondrial bioenergetics. Finally, recent studies have suggested a promising role for Nitric Oxide in preventing chlorine gas toxicity post-exposure, and for Nitrite (also released by the nanoparticles in this invention) in decreasing lung injury and mortality after inhalation of both chlorine and bromine.

Additional aspects of the invention are as follows:

1. A pharmaceutical formulation comprising either polymeric nanoparticles or polymeric nanoparticles encapsulated within cross-linked polymeric microparticles, wherein the polymeric nanoparticles carry a therapeutic agent suitable for treatment of a disorder loaded within them, for use in the treatment of the disorder, wherein the disorder is selected from chronic obstructive pulmonary disease, bronchial asthma, cystic fibrosis, chlorine inhalation, influenza, acute myocardial infarction and heart failure.

2. The formulation of aspect 1 which is an inhalable, dry powder pharmaceutical formulation.

3. The formulation of aspect 1 which is an oral pharmaceutical formulation.

4. The formulation of aspect 1 which is an injectable pharmaceutical formulation.

5. The formulation of any preceding aspect wherein the nanoparticles have a mean particle diameter of from 1 to 500 nm.

6. The formulation of any preceding aspect wherein the microparticles comprise a pH responsive carrier.

7. The formulation of any preceding aspect, wherein the cross-linked microparticles have a mean particle diameter from 1 to 5 µm for inhalable formulations, and from 1 to 500 µm, most preferably from 1 to 250 µm for oral formulations.

8. The formulation of any preceding aspect wherein the polymeric nanoparticles comprise a chitosan or a chitosan-derivative polymer.

9. The formulation of aspect 8 wherein the chitosan-derivative polymer is selected from chitosan-PEG, N-trimethyl chitosan, or a derivative of chitosan comprising a stearic acid, cholanic acid, phthaloyl, or butyl acrylate side chain.

10. The formulation of any of aspects 1 to 7 wherein the polymeric nanoparticles comprise poly (lactic-co-glycolic acid).

11. The formulation of any of aspects 1 to 7 wherein the polymeric nanoparticles comprise self-assembly amphiphilic chitosan derivatives.

12. The formulation of aspect 11 wherein the polymeric nanoparticles comprise self-assembly amphiphilic chitosan-PEG-Cholanic acid, or chitosan-PEG-Stearic acid orchitosan-PEG-Oleic acid.

13. The formulation of any preceding aspect wherein the nanoparticles are epithelially targeted.

14. The formulation of any preceding aspect wherein the polymeric nanoparticles have a moisture content, in the dry formulation, of less than 2%.

15. The formulation of any preceding aspect wherein the polymeric nanoparticles are produced via self assembly following sonication of amphiphilic polymer solutions.

16. The formulation of any preceding aspect wherein the cross-linked polymeric microparticles are cross-linked hydrogel polymeric microparticles.

17. The formulation of aspect 16 wherein the polymeric hydrogel microparticles are pH-responsive and comprise semi-interpenetrating polymeric networks (semi-IPNs) or full-IPNs.

18. The formulation of any preceding aspect wherein the microparticles comprise chitosan or a water soluble chitosan derivative, such as carboxymethyl and PEGylated derivatives.

19. The formulation of aspect 18 wherein the microparticles further comprise one or more polymers selected from hyaluronate, carrageenan and oligoguluronate.

20. The formulation of any preceding aspect wherein the microparticles incorporating nanoparticles are produced using spray-drying technique, spray gelation, or ionotropic gelation followed by lyophilization.

21. The formulation of any preceding aspect wherein the microparticles are swellable.

22. The formulation of aspect 21 wherein the microparticle is able to swell to at least 500% of the original (dry formulation) size.

23. The formulation of aspect 21 or 22 wherein the formulation is an inhalable dry powder formulation, and the microparticle is able to swell to a larger diameter within 10 minutes from administration to the lungs of a patient.

24. The formulation of any preceding aspect wherein the microparticle comprises less than 7.5% water when in the dry formulation.

25. The formulation of any preceding aspect wherein the therapeutic agent is a Nitric Oxide and/or Nitrite donor.

26. The use of a composition comprising polymeric nanoparticles or polymeric nanoparticles encapsulated within cross-linked polymeric microparticles, wherein the polymeric nanoparticles carry a therapeutic agent suitable for treatment of a disorder loaded within them, in the manufacture of a medicament for the treatment of a disorder, wherein the disorder is selected from chronic obstructive pulmonary disease, bronchial asthma, cystic fibrosis, chlorine inhalation, influenza, acute myocardial infarction and heart failure.

27. A method of treatment of a disorder, selected from chronic obstructive pulmonary disease, bronchial asthma, cystic fibrosis, chlorine inhalation, influenza and acute myocardial infarction, the method comprising administering a composition comprising polymeric nanoparticles or polymeric nanoparticles encapsulated within cross-linked polymeric microparticles, wherein the polymeric nanoparticles carry a therapeutic agent suitable for treatment of the diosrder loaded within them to a patient in need thereof, wherein the composition is administered by inhalation.

28. A pharmaceutical formulation comprising either polymeric nanoparticles or polymeric nanoparticles encapsulated within cross-linked polymeric microparticles, wherein the polymeric nanoparticles carry Nitric Oxide and/or a Nitrite donor loaded within them, and wherein the nanoparticles are targeted to the epithelium.

29. The use, method, or formulation of aspect 26, 27, or 28, wherein the microparticles comprise a pH responsive carrier.

30. An injectable pharmaceutical formulation comprising polymeric nanoparticles carrying a Nitric Oxide donor loaded within them, and wherein the nanoparticles are targeted to the epithelium.

31. An oral formulation comprising polymeric nanoparticles, polymeric microparticles, or polymeric nanoparticles encapsulated within smart pH-responsive cross-linked polymeric microparticles, wherein the polymeric nanoparticles carry Nitric Oxide and/or a Nitrite donor loaded within them, and wherein the pH-responsive microparticles are targeted to the intestine.

The invention claimed is:

1. A method of treatment of a disorder, selected from chronic obstructive pulmonary disease, bronchial asthma, cystic fibrosis, chlorine inhalation, influenza and acute myocardial infarction, the method comprising administering a pharmaceutical formulation comprising polymeric nanoparticles or polymeric nanoparticles encapsulated within cross-linked polymeric microparticles, wherein the polymeric nanoparticles carry a therapeutic agent suitable for treatment of the disorder loaded within them to a patient in need thereof, and wherein the microparticles comprise a pH responsive carrier.

2. The method of claim 1, wherein the pharmaceutical formulation is an inhalable, dry powder pharmaceutical formulation, an oral pharmaceutical formulation or an injectable pharmaceutical formulation.

3. The method of claim 1, wherein the nanoparticles have a mean particle diameter of from 1 to 500 nm and wherein the cross-linked microparticles have a mean particle diameter from 1 to 5 μm for inhalable formulations, and from 1 to 500 μm, most preferably from 1 to 250 μm for oral formulations.

4. The method of claim 1, wherein the polymeric nanoparticles comprise a chitosan or a chitosan-derivative polymer, wherein preferably the chitosan-derivative polymer is selected from chitosan-PEG, N-trimethyl chitosan, or a derivative of chitosan comprising a stearic acid, cholanic acid, phthaloyl, or butyl acrylate side chain.

5. The method of claim 1 wherein the polymeric nanoparticles comprise poly (lactic-co-glycolic acid).

6. The method of claim 1, wherein the polymeric nanoparticles comprise self-assembly amphiphilic chitosan derivatives, preferably wherein the polymeric nanoparticles comprise self-assembly amphiphilic chitosan-PEG-Cholanic acid, or chitosan-PEG-Stearic acid orchitosan-PEG-Oleic acid.

7. The method of claim 1, wherein the nanoparticles are epithelially targeted.

8. The method of claim 2, wherein the polymeric nanoparticles have a moisture content, in the dry formulation, of less than 2%.

9. The method of claim 1, wherein the polymeric nanoparticles are produced via self assembly following sonication of amphiphilic polymer solutions.

10. The method of claim 1, wherein the cross-linked polymeric microparticles are cross-linked hydrogel polymeric microparticles, preferably wherein the polymeric hydrogel microparticles are pH-responsive and comprise semi-interpenetrating polymeric networks (semi-IPNs) or full-IPNs.

11. The method of claim 1, wherein the microparticles comprise chitosan or a water soluble chitosan derivative, such as carboxymethyl and PEGylated derivatives.

12. The method of claim 11, wherein the microparticles further comprise one or more polymers selected from hyaluronate, carrageenan and oligoguluronate.

13. The method of claim 1, wherein the microparticles incorporating nanoparticles are produced using spray-drying technique, spray gelation, or ionotropic gelation followed by lyophilization.

14. The method of claim 1, wherein the microparticles are swellable, wherein preferably the microparticle is able to swell to at least 500% of the original (dry formulation) size.

15. The method of claim 2, wherein the formulation is an inhalable dry powder formulation, and the microparticle is able to swell to a larger diameter within 10 minutes from administration to the lungs of a patient.

16. The method of claim 2, wherein the microparticle comprises less than 7.5% water when in the dry formulation.

17. The method of claim 1, wherein the therapeutic agent is a Nitric Oxide and/or Nitrite donor.

18. A method of treatment of a disorder, selected from chronic obstructive pulmonary disease, bronchial asthma, cystic fibrosis, chlorine inhalation, influenza and acute myocardial infarction, the method comprising administering a pharmaceutical formulation comprising polymeric nanoparticles or polymeric nanoparticles encapsulated within cross-linked polymeric microparticles, wherein the polymeric nanoparticles carry a therapeutic agent suitable for treatment of the disorder loaded within them to a patient in need thereof, and wherein the nanoparticles are epithelially targeted.

19. A method of treatment of a disorder, selected from chronic obstructive pulmonary disease, bronchial asthma, cystic fibrosis, chlorine inhalation, influenza and acute myocardial infarction, the method comprising administering a pharmaceutical formulation comprising polymeric nanoparticles or polymeric nanoparticles encapsulated within cross-linked polymeric microparticles, wherein the polymeric nanoparticles carry a therapeutic agent suitable for treatment of the disorder loaded within them to a patient in need thereof, and wherein the therapeutic agent is a Nitric Oxide and/or Nitrite donor, and wherein the therapeutic agent is a Nitric Oxide and/or Nitrite donor.

* * * * *